United States Patent [19]

Asbell

[11] 4,178,071
[45] Dec. 11, 1979

[54] MAGNIFYING CYLINDER FOR INSULIN SYRINGE

[76] Inventor: Burma B. Asbell, 1114 NE. 8th Ave., Gainesville, Fla. 32601

[21] Appl. No.: 845,484

[22] Filed: Oct. 26, 1977

[51] Int. Cl.² .............................................. G02B 27/02
[52] U.S. Cl. ............................... 350/116; 128/218 R; 73/372; 350/191
[58] Field of Search .............................. 350/115, 116; 128/221-222, 172, 128, 213, 215, 216, 224, 218 R, 172; 73/372, 373, 425

[56] References Cited

U.S. PATENT DOCUMENTS

| 2,389,282 | 11/1945 | Stegeman | 73/372 |
| 2,586,581 | 2/1952 | Tschischeck | 73/372 UX |
| 3,304,784 | 2/1967 | Asher | 73/425.4 P |
| 3,762,799 | 10/1973 | Shaprio | 350/116 |
| 3,855,866 | 12/1974 | Klinger et al. | 73/372 |

Primary Examiner—John K. Corbin
Assistant Examiner—B. W. de los Reyes
Attorney, Agent, or Firm—Robert D. Farkas

[57] ABSTRACT

A magnifying cylinder for insulin syringe utilizes a tubular body having at least a portion thereof transparent and configured to reside along the liquid containing portion of a hypodermic syringe. The transparent portion of the body extends along the length thereof and has the property of magnifying the scale on the length of the liquid containing portion of the syringe. A band is clasped frictionally on the outside surface of the tubular portion and carries a magnifying lens thereon positioned over the transparent portion of the tubular body. The lens apparatus is provided with an indicia line indicating the level to which liquid is to filled within the syringe. In one embodiment a pair of semi-annular grooves are disposed in the body portion so as to fix the band at a preferred location. In another embodiment the band may be positioned selectively along the length of the body portion. The body portion is provided with a longitudinal slit insuring grasping thereof to the cylindrical surface of the syringe.

9 Claims, 5 Drawing Figures

U.S. Patent           Dec. 11, 1979           4,178,071

# MAGNIFYING CYLINDER FOR INSULIN SYRINGE

BACKGROUND OF THE INVENTION

1. The Field of the Invention

This invention relates to magnifying devices and filling indicating apparatus useful with hypodermic syringes and more particularly to that class adapted to be transferred from syringe to syringe at the will of the user.

2. Description of the Prior Art

The prior art abounds with magnifying devices suitable for use with medical apparatus. U.S. Pat. No. 3,855,866 issued Dec. 24, 1974 to J. F. Klinger et al teaches a readout device for use with a thermometer for facilitating determination of the thermometer reading and also to retain the determined indication notwithstanding a subsequent change in the indicator reading. The readout means may define a magnifying lens for facilitating the readout and includes resilient gripping means for retaining the readout means adjustably on the thermometer stem. A readout means may be adjusted while the thermometer is in the patient's body orifice. The thermometer includes a metal bulb secured to one end of the stem to provide a sealed connection therewith. This apparatus provides an indicia line associated with the magnifying lens so as to increase the capability of determining the readout at a later point in time, following taking the temperature of the patient's body. Such apparatus however, is secured to the thermometer in a pseudopermanent manner thereby precluding its use with disposable medical instruments.

U.S. Pat. No. 3,052,158 issued Sept. 4, 1962 to A. W. Sonni discloses a combination of a clinical thermometer and a magnifying case. A case is provided, being fabricated from a transparent material and having a convex lens portion comprising a portion of the walls thereof. A thermometer may be inserted within the case in a preferred location, capped therein by a removable cap portion so as to selectively position the readout scale of the thermometer below the magnifying portion of the case. In use, the patient's temperature is first taken; the thermometer is then stored within the case so as to permit the user to more conveniently read the readout scale of the thermometer. However, such apparatus requires that the thermometer be removed after use for cleaning purposes before the apparatus is stored therewithin again. The means required to position the readout scale at the preferred angular relationship to the magnifying portion of the case requires careful alignment and hence makes such apparatus difficult to use.

U.S. Pat. No. 2,389,282 issued Nov. 20, 1945 to R. F. E. Steggman describes a convex lens portion having a pair of outwardly extending wings from the end thereof, each wing-like portion is provided with a hole. Both holes are coaxially aligned and adapted to frictionally engage the side thermometer. In use, the magnifying portion of the apparatus defined between the wing portions thereof, is positioned over the readout scale of the thermometer. Such lens portion may be moved to preferential locations so as to facilitate the reading of the thermometer apparatus. The Steggman disclosure, however, though providing an indicia line extending transverse to the length of the thermometer, fails to position the magnifying device in a convenient referenced fashion to a preferred location along the length of the medical device on which it is employed. Thus, Steggman, as well as the aforementioned other patents, each fail to teach an apparatus which enables the user to adjust some function of the device employing the same to a preset level. Rather, these apparatuses simply allow the user to readout a function presented to the apparatus, namely the level of mercury indicative of body temperature.

SUMMARY OF THE INVENTION

A primary object of the present invention is to provide an indicator device which is useful in monitoring the amount of liquid present in a syringe whilst permitting the user to refer to a marking useful in selecting the amount of liquid intended to be confined within the syringe.

Another object of the present invention is to provide a syringe magnifying apparatus which enables the user to magnify the entire length of the liquid confining portion of the syringe, thereby enabling the user to more readily determine the amount of liquid captured therewithin regardless of the quantity of liquid contained within the cavity of the syringe.

Still another object of the present invention is to provide a lens magnification device which produces increased magnification in the area where the liquid level is desired to be maintained.

Yet another object of the present invention is to provide an adjustable indicia line which may be positioned at any preferred location along the body of the syringe, thereby enabling the user to utilize external markings, adjustable in nature, to readily and conveniently fill the syringe accurately with liquid.

A further object of the present invention is to provide a magnifying apparatus which may be installed and removed on a syringe with great ease.

Another object of the present invention is to provide a reference line that may be selectively positioned at one location or, if desired, positioned in the neighborhood thereof, so as to remind the user of the preferred amount of liquid to be accumulated in the syringe without having to refer to any other markings on the syringe body.

Still another object of the present invention is to provide a volumetric measuring device which is devoid of scales, thereby suitable for use without requiring knowledge in the use of such scales.

Yet another object of the present invention is to provide a magnification system for syringes, useful with patients who have visual deficiencies.

A further object of the present invention is to provide a syringe that is inexpensive in nature, inexpensive in construction, rugged in nature, simple to use and lightweight.

Patients who require the use of insulin, in order to control a diabetic condition, are often required to utilize extremely thin hypodermic syringes on a daily basis. With the advent of disposable syringes, scale markings, usually in the form of printing, disposed on the surface of the body of the syringe, are difficult to read, not only because of the size of the syringe but also because such markings are of substantial line thickness. Many advanced diabetic patients also suffer from sight deficiencies, thus increasing the difficulty in utilizing disposable insulin-type syringes. Aged patients, as well as small children, find it difficult to interpret the scale markings and therefore often times inject improper quantities of the insulin preparation they so vitally require in accurate amounts. In short, the problem facing a patient is to determine the exact amount of liquid contained within the body of the syringe and hopefully, after making such determination, adjust the volume of liquid to the required amount. Remembering such amount, if in terms of a scale reading, makes the task all the more difficult.

The present invention contemplates these difficulties and resolves same by providing an apparatus which allows the user to read the amount of liquid contained within the syringe in a magnified fashion and to adjust the volume of liquid in the syringe to a supermagnified indicia line, selectively positioned at exactly the right location so as to procure thereby the exact measure of the volume of liquid required. In one embodiment, the present invention pseudo-permanently marks the location of the exact preferred position of the plunger of the syringe, thereby permitting the user to totally avoid the need to remember anything about the syringe filling operation. The present invention also contemplates the need to have the apparatus thereof to be easily installed and removed from such disposal syringes and takes into account that the apparatus must be installed in a preferred relationship to the body of the syringe so as to insure that the volume of liquid selected to be contained within the syringe is exactly correct in amount. The apparatus of the present invention is sterilizable, inexpensive to manufacture and virtually indestructible. Small children or the infirm can easily utilize the present invention in a daily routine without confusion and without assistance from others.

These objects as well as other objects of the present invention, will become more readily apparent after reading the following description of the accompanying drawings.

DESCRIPTION OF THE PREFERRED EMBODIMENT

Figure 1:
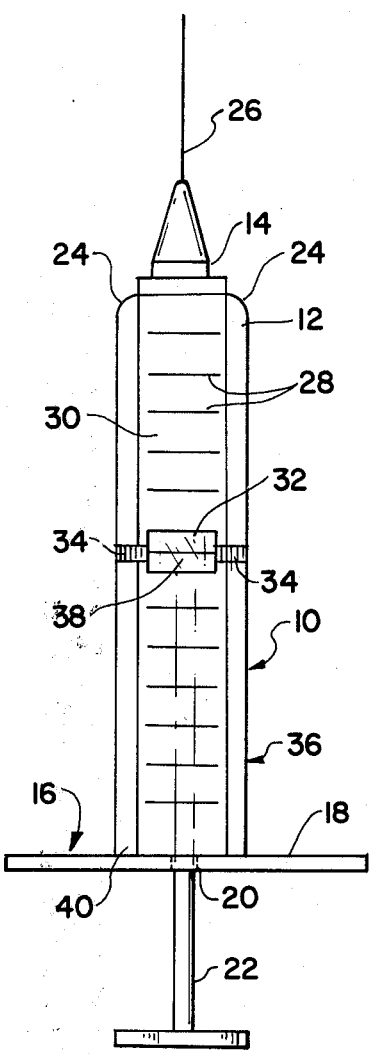
FIG. 1 is the side elevation view of the present invention shown installed on a hypodermic syringe.

The structure and method of fabrication of the present invention is applicable to an elongated tubing, rigid in nature, and having a portion thereof, extending along the length thereof, transparent. If desired, the entire tubing portion may be transparent. Such tubing portion may be constructed from a plastic material, such as Cellulose Acetate Butyrate. The passageway of the tubing is cylindrical in nature. The outside surfaces of the tubing may be cylindrical in nature, or if desired, may have an elongated bulbous-like protrusion extending along a portion of the surface running parallel to the longitudinal axis of the tubing. In either case, the tubing acts as a magnifying lens for the body portion of a hypodermic syringe, inserted within the passageway portions thereof. An elongated slit is disposed communicating between the exterior surface of the tubing and the passageway portion thereof, extending parallel to the longitudinal axis of the tubing. Such slit is positioned on an opposite side of the tubing when such tubing is provided having a bulbous protrusion. If desired, the regions of the tubing disposed adjacent the slit, either within the interior passageway of the tubing, or on a portion of the exterior surface thereof, may be opaque. This is accomplished by the inherent properties of the plastic-like tubing itself, or if desired, by coating such surfaces with a suitable opaque material, such as paint. Such opaque areas assist the user in more readily visualizing the liquid level confined within the body of the syringe. Since insulin is usually colorless, a darkened background is useful, but not necessary.

A pair of semi-rigid straps are provided, each having an arcuate shape, and each being attached to a rectangularly shaped lens having oppositely disposed concave and convex surfaces. The straps are aligned so as to frictionally engage the exterior surface of the tubing whilst permitting the strap and lens apparatus to be repositioned to selected locations along the length of the tubing. In the case, where a tubing is provided having a protrusion, the lens curvature is adapted to accommodate the curvature of the exterior surface of the protrusion. In the case where the tubing is cylindrical in nature, the concave surface is adapted to contact the cylindrical exterior surface of the tubing, and the convex surface, opposite the tube, is curved so as to further magnify the surface of the body portion of the syringe disposed within the tubing. The lens portion of the slideable lens is provided having an indicia line disposed thereon so as to extend transverse to the longitudinal axis of the passageway of the tubing. Such indicia line may be formed by scribing, printing, molding or any other similar operation. The strap-movable lens portion of the present invention is adapted to frictionally clamp to the exterior surface of the tubing portion and to be moved slideably therealong at the will of the user, when the tubing portion is frictionally clamped to the exterior surface of the hypodermic syringe.

One end of the tubing portion may be provided having an external beveled edge so as to indicate to the user that such end is to be disposed on the body of the syringe adjacent the hypodermic needle end thereof.

A pair of arcuately shaped grooves may be disposed aligned annularly along the exterior surface of the tubing portion of the present invention. Such grooves serve the function of permitting the strap portions of the slideable lens apparatus to be engaged therewithin thereby positioning the movable lens apparatus at a preferred location, as well as the indicia line associated therewith. When such grooves are employed, the user no longer requires any knowledge of scale usage and simply relies upon the position of the indicia line to select the meniscus level of the fluid within the body of the syringe. In this construction, when the apparatus is transferred to another hypodermic syringe, the user need not set or control any apparatus in order to know exactly where the liquid level is required to be set, within the syringe, for an exact measurement of the dosage of medicament required.

The strap portions, as well as the lens portions, may be unitary in nature, if desired. The material comprising the straps and the lens, whether unitary or not, may be any rigid or semi-rigid plastic material, such as in the acetate family or the like. When the pair of grooves are used in conjunction with the noncylindrical shaped tubing embodiment, such grooves are positioned so as to preferentially locate the movable lens portion of the present invention disposed over the protrusion portion of the tubing. Alternatively, positioning the movable lens portion on another area of the tubing enables the user to quickly determine the level of liquid along the elongated stationary lens portion of the tubing and then by rotating the syringe, to accurately determine the level of liquid in the zone supermagnified by the movable lens apparatus.

Now referring to the figures, and more particularly to the embodiment illustrated in FIG. 1 showing the present invention 10 shown having a tubing portion 12 installed residing along the length of a body portion 14 of syringe 16. Winged-like extension 18 extends outwardly from body portion 14 and is provided with opening 20, in conventional fashion, permitting rod 22 to be installed therein. Rounded corners 24 are shown disposed adjacent hypodermic needle end 26 of syringe body 14. Indicia lines 28 are visually accessible through transparent region 30 of tubing 12 and are carried on body portion 14 of the syringe. Movable lens 32 is shown carried by straps 34, clasped to exterior surface 36 of tubing 12. Indicia line 38 is visually accessible through movable lens 32 and is disposed transverse to the longitudinal axis of syringe body 14. End 40, of tubing 12, shown opposite to rounded corners 24, is disposed adjacent winged portion 18 and in touching engagement therewith. Liquid, not shown, contained within body portion 14, is visible through transparent region 30 and supermagnified by moving lens 32.

Figure 2:
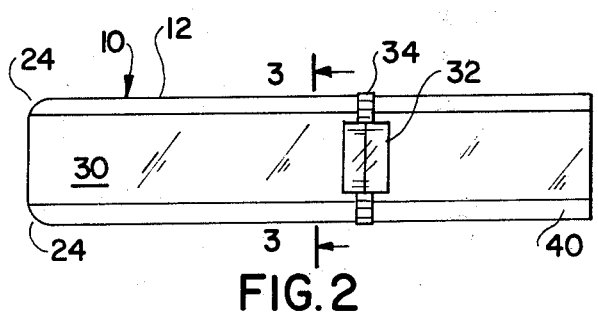
FIG. 2 is the side elevation view of the present invention.

FIG. 2 illustrates present invention 10 shown having transparent area 30 extending along the length thereof disposed between end 40 and rounded corners 24. Straps 34 and movable lens 32 are shown superimposed over transparent area 30. If desired, tubing 12 may be transparent throughout its length and its girth. Furthermore, movable lens 32 may be positioned at any location other than transparent region 30.

Figure 3:
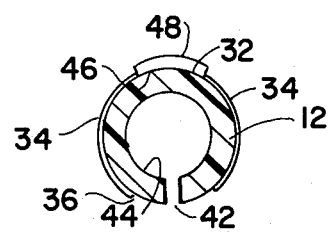
FIG. 3 is the side elevation cross-sectional view, taken along line 3—3, viewed in the direction of arrows 3—3, of the apparatus shown in FIG. 2.

FIG. 3 illustrates tubing portion 12 having slit 42. Such slit communicates along the entire length of tubing 12 so as to permit interior surface 44 to expand so as to snugly engage the exterior surface of body portion 14, shown in FIG. 1. Movable lens 32 is shown having a concave surface 46 disposed opposite to a convex surface 48 thereof. As shown, tubing 12 is cylindrical in nature. In this embodiment surface 46 is arcuately shaped having a complementary curve so as to follow the curvature of exterior surface 36. Surface 48, may be parallel to surface 46, as shown however, surface 48 may be of any desired convex shape so as to provide a supermagnification of surface 44, greater than the magnification provided by tubing 12.

Figure 4:
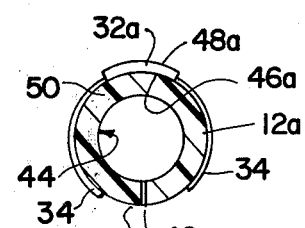
FIG. 4 is the side elevation cross-sectional view of another embodiment of the apparatus shown in FIG. 3.

FIG. 4 illustrates tubing 12a shown having a bulbous area 50 disposed opposite the location of slit 42. Such bulbous area provides greater magnification of surface 44 in the regions adjacent thereto than the magnification provided by cylindrical tubing 12, shown in FIG. 3. It is to be noted that surface 46a of movable lens 32a is configured to be complementary shaped to the outermost surface of protrusion 50. However, should movable lens 32a be desired to be installed in a location other than superimposed over protrusion 50, surface 46a may be complementary shaped to the exterior surface 36a thereat. Exterior surface 48a, of movable lens 32a, may be shaped so as to provide a lens of suitable magnification dependent upon the angular location of such lens.

Figure 5:
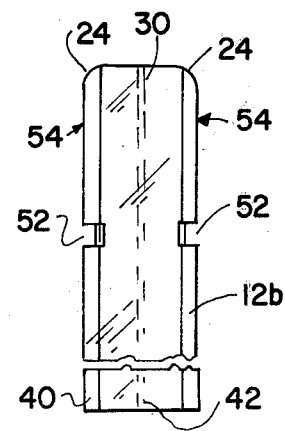
FIG. 5 is a side elevation view of an alternate embodiment of the apparatus shown in FIG. 2.

FIG. 5 illustrates an alternate embodiment 12b of tubing 12, shown in FIG. 2. A pair of semi-annular notches 52 are shown disposed annularly and transverse to the longitudinal axis of tubing 12b. Such notches are adapted to permit straps 34, shown in FIG. 1, to reside therein. This permits movable lens 32, shown in FIG. 1, to be positioned at any preferred location relative to end 40 thereby accurately locating indicia line 38, shown in FIG. 1. Transparent region 30 is shown intermediate the ends of grooves 52. Opaque regions 54, if employed, are shown disposed on either side of transparent region 30 and encircling the rear regions of body portion 12b adjacent the location of slit 42 therein. Such opaque regions may be employed in the embodiment illustrated in FIGS. 2 and 4, if desired.

One of the advantages of the present invention is an indicator device which is useful in monitoring the amount of liquid present in a syringe whilst permitting the user to refer to a marking useful in selecting the amount of liquid intended to be confined within the syringe.

Another advantage of the present invention is a syringe magnifying apparatus which enables the user to magnify the length of the liquid confining portion of the syringe, thereby enabling the user to more readily determine the amount of liquid captured therewithin regardless of the quantity of liquid contained within the cavity of the syringe.

Still another advantage of the present invention is to provide a lens magnification device which produces increased magnification in the area where the liquid level is desired to be maintained.

Yet another advantage of the present invention is to provide an adjustable indicia line which may be positioned at any preferred location along the body of the syringe, thereby enabling the user to utilize external markings, adjustable in nature, to readily and conveniently fill the syringe accurately with liquid.

A further advantage of the present invention is to provide a magnifying apparatus which may be installed and removed on a syringe with great ease.

Another advantage of the present invention is to provide a reference line that may be selectively positioned at one location or, if desired, positioned in the neighborhood thereof, so as to remind the user of the preferred amount of liquid to be accumulated in the syringe without having to refer to any other markings on the syringe body.

Still another advantage of the present invention is to provide a volumetric measuring device which is devoid of scales, thereby suitable for use without requiring knowledge in the use of such scales.

Yet another advantage of the present invention is to provide a magnification system for syringes, useful with patients who have visual deficiencies.

A further advantage of the present invention is to provide a syringe that is inexpensive in nature, inexpensive in construction, rugged in nature, simple to use and lightweight.

Thus, there is disclosed in the above description and in the drawings, an embodiment of the invention which fully and effectively accomplishes the objects thereof. However, it will become apparent to those skilled in the art, how to make variations and modifications to the instant invention. Therefore, this invention is to be limited, not by the specific disclosure herein, but only by the appending claims.

The embodiment of the invention in which an exclusive privilege or property is claimed are defined as follows: